US010314703B2

(12) United States Patent
Maimon et al.

(10) Patent No.: US 10,314,703 B2
(45) Date of Patent: Jun. 11, 2019

(54) CYLINDRICAL IMPLANT AND BALLOON

(71) Applicant: Edwards Lifesciences Corporation, Irvine, CA (US)

(72) Inventors: David Maimon, Haifa (IL); Michael R. Bialas, Lake Forest, CA (US); Mindy Lee Ann Black, Huntington Beach, CA (US); Tamir S. Levi, Moshav Ein HaEmek (IL); Linda Thai, Mission Viejo, CA (US); Yidong M. Zhu, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 289 days.

(21) Appl. No.: 15/263,204

(22) Filed: Sep. 12, 2016

(65) Prior Publication Data
US 2017/0079793 A1 Mar. 23, 2017

Related U.S. Application Data

(60) Provisional application No. 62/221,541, filed on Sep. 21, 2015.

(51) Int. Cl.
*A61F 2/24* (2006.01)
*A61F 2/958* (2013.01)

(52) U.S. Cl.
CPC .......... *A61F 2/2433* (2013.01); *A61F 2/2418* (2013.01); *A61F 2/958* (2013.01); *A61F 2230/001* (2013.01)

(58) Field of Classification Search
CPC ...... A61F 2/2418; A61F 2/2409; A61F 2/243; A61F 2/2436; A61F 2/2433; A61F 2/2427
See application file for complete search history.

(56) References Cited

U.S. PATENT DOCUMENTS 3,755,823 A 9/1973 Hancock
4,035,849 A 7/1977 Angell et al.
(Continued)

FOREIGN PATENT DOCUMENTS

DE 19532846 A1 3/1997
DE 19546692 A1 6/1997
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
H.R. Andersen "History of Percutaneous Aortic Valve Prosthesis," Herz No. 34. pp. 343-346. 2009.
(Continued)

*Primary Examiner* — Tuan V Nguyen
(74) *Attorney, Agent, or Firm* — Meunier Carlin & Curfman LLC; Joel B. German; AnneMarie Kaiser

(57) ABSTRACT

Disclosed herein are embodiments of a balloon shaped to have one or more enlarged regions to selectively increase expansion forces on an implant. For example, the balloon may have a central portion that is enlarged to exert more force on the center of a stent-mounted prosthetic heart valve. This overcomes the stent-mounted prosthetic heart valve's tendency to expand with flared ends. This forms a more cylindrical or barrel shaped stent frame during expansion of the balloon—reducing or eliminating the instance wherein the cylindrical stent frame has flared ends. Alternatively, the balloon may have conical flares placed to cause or enhance flared ends of the cylindrical implant to enhance its anchoring capabilities.

19 Claims, 12 Drawing Sheets

(56) References Cited

U.S. PATENT DOCUMENTS

| | | | |
|---|---|---|---|
| 4,777,951 A | 10/1988 | Cribier et al. |
| 4,787,899 A | 11/1988 | Lazarus |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,282,847 A | 2/1994 | Trescony et al. |
| 5,370,685 A | 12/1994 | Stevens |
| 5,411,552 A | 5/1995 | Andersen et al. |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,665,115 A | 9/1997 | Cragg |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,925,063 A | 7/1999 | Khosravi |
| 6,027,525 A | 2/2000 | Suh et al. |
| 6,168,614 B1 | 1/2001 | Andersen et al. |
| 6,221,091 B1 | 4/2001 | Khosravi |
| 6,245,102 B1 | 6/2001 | Jayaraman |
| 6,302,906 B1 | 10/2001 | Goicoechea et al. |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,468,302 B2 * | 10/2002 | Cox | A61F 2/91 623/1.15 |
| 6,482,228 B1 | 11/2002 | Norred |
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,767,362 B2 | 7/2004 | Schreck |
| 6,830,584 B1 | 12/2004 | Seguin |
| 6,878,162 B2 | 4/2005 | Bales et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,018,408 B2 | 3/2006 | Bailey et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,655,034 B2 | 2/2010 | Mitchell et al. |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,167,932 B2 | 5/2012 | Bourang et al. |
| 8,449,606 B2 | 5/2013 | Eliasen et al. |
| 8,652,203 B2 | 2/2014 | Quadri et al. |
| 2002/0026094 A1 | 2/2002 | Roth |
| 2002/0032481 A1 | 3/2002 | Gabbay |
| 2002/0077690 A1 * | 6/2002 | Wang | A61F 2/958 623/1.11 |
| 2002/0138135 A1 | 9/2002 | Duerig et al. |
| 2003/0050694 A1 | 3/2003 | Yang et al. |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0075728 A1 | 4/2005 | Nguyen et al. |
| 2005/0096736 A1 | 5/2005 | Osse et al. |
| 2005/0188525 A1 | 9/2005 | Weber et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0025857 A1 | 2/2006 | Bergheim et al. |
| 2006/0058872 A1 | 3/2006 | Salahieh et al. |
| 2006/0149350 A1 | 7/2006 | Patel et al. |
| 2006/0183383 A1 | 8/2006 | Asmus et al. |
| 2007/0005131 A1 | 1/2007 | Taylor |
| 2007/0010876 A1 | 1/2007 | Salahieh et al. |
| 2007/0010877 A1 | 1/2007 | Salahieh et al. |
| 2007/0112422 A1 | 5/2007 | Dehdashtian |
| 2007/0162102 A1 | 7/2007 | Ryan et al. |
| 2007/0203503 A1 | 8/2007 | Salahieh et al. |
| 2007/0203575 A1 | 8/2007 | Forster et al. |
| 2007/0213813 A1 | 9/2007 | Von Segesser et al. |
| 2007/0265700 A1 | 11/2007 | Eliasen et al. |
| 2008/0114442 A1 | 5/2008 | Mitchell et al. |
| 2008/0125853 A1 | 5/2008 | Bailey et al. |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0312827 A1 * | 12/2009 | Stapleton | A61M 25/0108 623/1.11 |
| 2009/0319037 A1 | 12/2009 | Rowe et al. |
| 2010/0049313 A1 | 2/2010 | Alon et al. |
| 2010/0168844 A1 | 7/2010 | Toomes et al. |
| 2010/0198347 A1 | 8/2010 | Zakay et al. |
| 2011/0015729 A1 | 1/2011 | Jimenez et al. |
| 2012/0123529 A1 | 5/2012 | Levi et al. |
| 2012/0259409 A1 | 10/2012 | Nguyen et al. |
| 2012/0303110 A1 * | 11/2012 | Anderson | A61F 2/958 623/1.11 |
| 2013/0023985 A1 | 1/2013 | Khairkhahan et al. |
| 2013/0190857 A1 | 7/2013 | Mitra et al. |
| 2013/0274873 A1 | 10/2013 | Delaloye et al. |
| 2013/0317598 A1 | 11/2013 | Rowe et al. |
| 2013/0331929 A1 | 12/2013 | Mitra et al. |
| 2014/0194981 A1 | 7/2014 | Menk et al. |
| 2014/0200661 A1 | 7/2014 | Pintor et al. |
| 2014/0277417 A1 | 9/2014 | Schraut et al. |
| 2014/0277419 A1 | 9/2014 | Garde et al. |
| 2014/0277424 A1 | 9/2014 | Oslund |
| 2014/0330372 A1 | 11/2014 | Weston et al. |
| 2014/0343671 A1 | 11/2014 | Yohanan et al. |
| 2014/0350667 A1 | 11/2014 | Braido et al. |
| 2015/0073545 A1 | 3/2015 | Braido |
| 2015/0073546 A1 | 3/2015 | Braido |
| 2015/0141917 A1 * | 5/2015 | Tilson | A61F 2/958 604/103.07 |

FOREIGN PATENT DOCUMENTS

| | | |
|---|---|---|
| DE | 19857887 A1 | 7/2000 |
| DE | 19907646 A1 | 8/2000 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1796597 A2 | 6/2007 |
| FR | 2788217 A1 | 7/2000 |
| FR | 2815844 A1 | 5/2002 |
| SU | 1271508 A1 | 11/1986 |
| WO | 9117720 A1 | 11/1991 |
| WO | 9301768 A1 | 2/1993 |
| WO | 9829057 A1 | 7/1998 |
| WO | 9940964 A1 | 8/1999 |
| WO | 9947075 A1 | 9/1999 |
| WO | 0041652 A1 | 7/2000 |
| WO | 0047139 A1 | 8/2000 |
| WO | 0149213 A2 | 7/2001 |
| WO | 0154625 A1 | 8/2001 |
| WO | 0162189 A1 | 8/2001 |
| WO | 0164137 A1 | 9/2001 |
| WO | 0176510 A2 | 10/2001 |

(56) References Cited

FOREIGN PATENT DOCUMENTS

| | | |
|---|---|---|
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 05/034812 | 4/2005 |
| WO | 2005084595 A1 | 9/2005 |
| WO | 05/102015 | 11/2005 |
| WO | 06/111391 | 10/2006 |
| WO | 2006127089 A1 | 11/2006 |
| WO | 2006138173 A2 | 12/2006 |
| WO | 2007047488 A2 | 4/2007 |
| WO | 2007067942 A1 | 6/2007 |
| WO | 2007097983 A2 | 8/2007 |
| WO | 2008005405 A2 | 1/2008 |
| WO | 2008015257 A2 | 2/2008 |
| WO | 2008091515 A2 | 7/2008 |
| WO | 2009033469 A1 | 3/2009 |
| WO | 2010121076 A2 | 10/2010 |

OTHER PUBLICATIONS

Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.

* cited by examiner

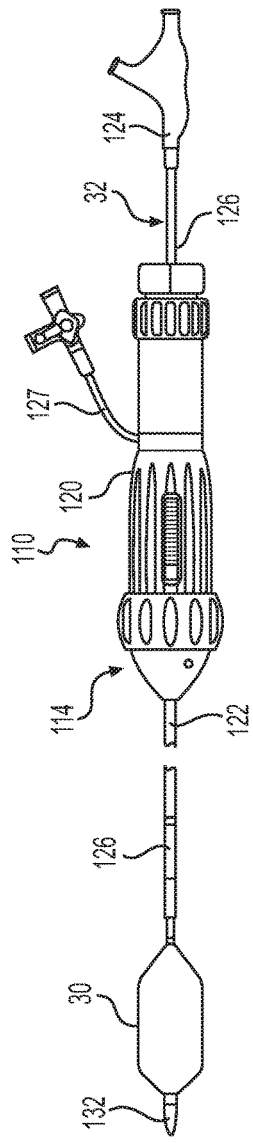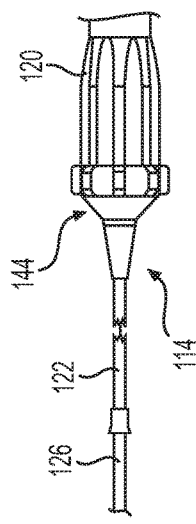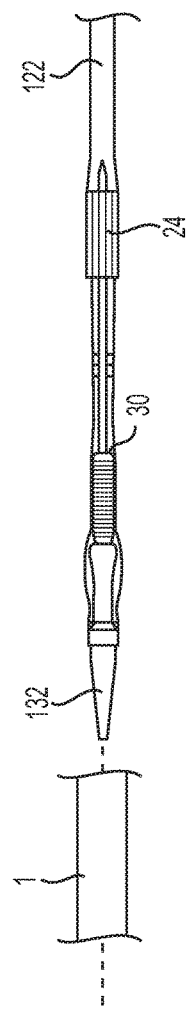
FIG. 2A
FIG. 2B
FIG. 2C

| PRESSURE (ATM) | MIDDLE DIAMETER (mm) | INFLOW DIAMETER (mm) | OUTFLOW DIAMETER (mm) | M/I | M/O |
|---|---|---|---|---|---|
| 3.5 | 19.95 | 21.64 | 19.76 | -8% | 1% |
| 4 | 22.29 | 22.15 | 21.06 | 1% | 6% |
| 4.5 | 22.68 | 22.77 | 21.85 | 0% | 4% |
| 5 | 22.86 | 22.75 | 22.52 | 0% | 2% |
| 6 | 23.81 | 23.45 | 22.42 | 2% | 6% |
*FIG. 8*
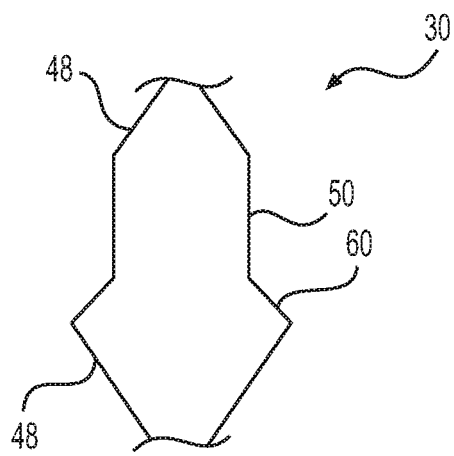
*FIG. 9*
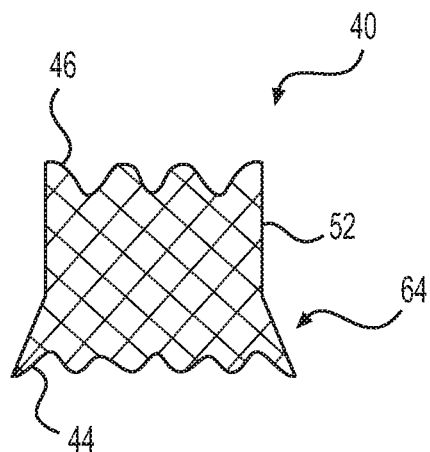
*FIG. 10*

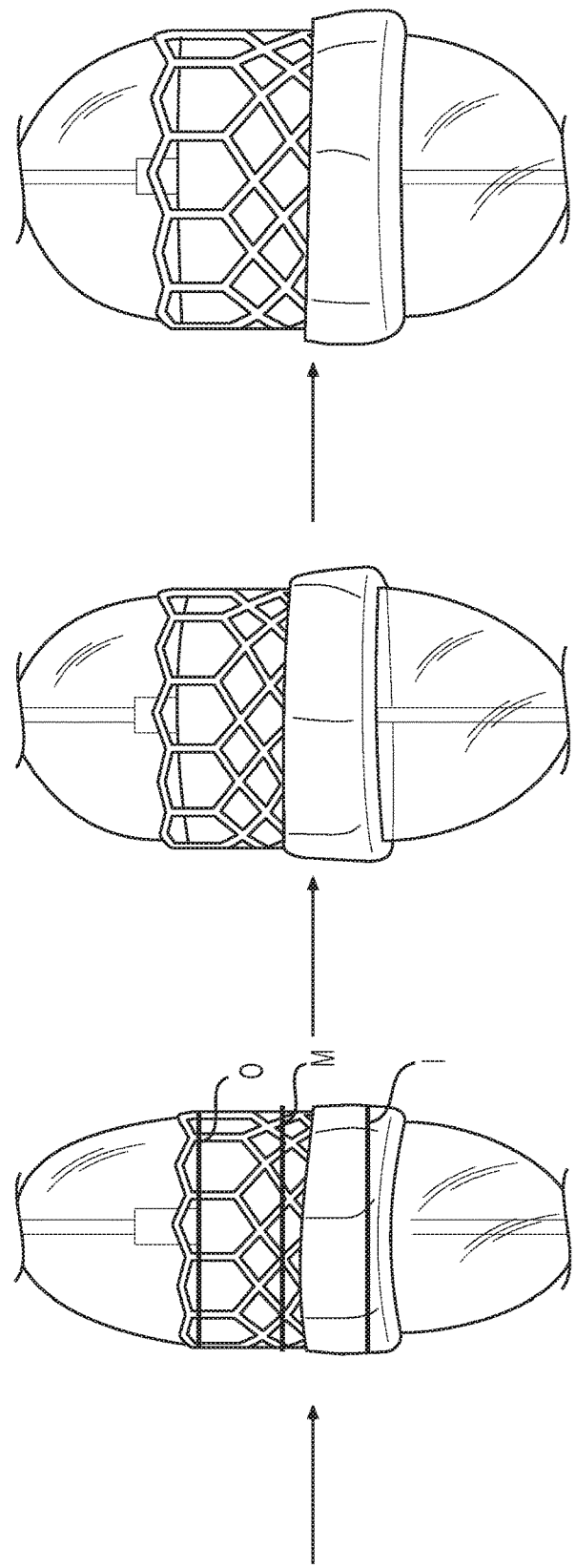

CYLINDRICAL IMPLANT AND BALLOON

RELATED APPLICATIONS

This application claims the benefit of U.S. Provisional Application No. 62/221,541, filed Sep. 21, 2015, entitled "Cylindrical Implant and Balloon," the disclosure of which is hereby incorporated by reference in its entirety.

FIELD OF THE INVENTION

The disclosed devices and methods relate generally to implanting prosthetics in a patient, and in particular balloon catheters for delivering and expanding stent-mounted prosthetic heart valves.

BACKGROUND

Heart valve disease is a serious problem that involves the malfunction of one or more valves of the heart. The malfunction can manifest itself in a variety of manners. For example, valve stenosis is the calcification or narrowing of a native heart valve. As a result, the native heart valve is not able to completely open and blood flow through the native valve is impeded or restricted. Another example of heart valve disease is valve insufficiency. Valve insufficiency is the failure of a native heart valve to close properly to prevent leaking, or backflow, of blood through the valve.

One method of treating valve disease is to replace the native valve with an artificial or prosthetic heart valve. Prosthetic heart valves include stent-mounted soft tissue heart valves that are delivered using a catheter. For example, the prosthetic heart valve may be mounted on the balloon of the balloon catheter. The balloon catheter is advanced to the native heart valve site. Then the balloon is expanded to release or expand the stent supporting the heart valve into place within the native heart valve. The balloon is then deflated and the balloon catheter withdrawn.

Problems have arisen where the stent supporting the tissue valve is expanded in a non-cylindrical manner, for example, when the ends of the stent flare outwards into a dog-bone shape. The flared ends can negatively influence valve performance or can damage the tissue surrounding the implanted valve.

Accordingly, a need exists for improved prosthetic heart valves and/or balloon catheters that deliver them to reduce or eliminate the flared ends of the valves.

SUMMARY

Disclosed herein are embodiments of a balloon for expanding a generally cylindrical implant—such as a prosthetic heart valve—wherein the balloon is shaped to have one or more enlarged regions to selectively increase expansion forces on the implant. For example, in one embodiment, the balloon may have a central portion that is enlarged to exert more force on the center of a stent-mounted prosthetic heart valve. This overcomes the stent-mounted prosthetic heart valve's tendency to expand with flared ends. This forms a more cylindrical or barrel shaped stent frame during expansion of the balloon—reducing or eliminating the instance wherein the cylindrical stent frame has flared ends. The flared ends can interfere with implantation or post-implantation function. Alternatively, the balloon may have conical flares placed to cause or enhance flared ends of the cylindrical implant to enhance its anchoring capabilities. In some stent-mounted prosthetic heart valves a flared end will spare wear on the soft-tissue leaflets.

A system is included in one embodiment, the system comprising an implant and a balloon. The implant has a generally cylindrical stent frame with an axial opening. The stent frame has an inflow end defining an inflow diameter, an outflow end defining an outflow diameter and a central region defining a central diameter, the central region being between the inflow end and outflow end. The balloon extends through the axial opening and is configured to expand and exert a radially directed force against the stent frame so that the outflow diameter and inflow diameter are equal to or smaller than the central diameter in an at least partially (e.g., partially or fully) expanded condition. The central diameter of the stent frame can be from 0% to 6% larger than either the inflow or the outflow diameter of the stent frame in the at least partially expanded condition and at a pressure in the balloon of at least 4 atmospheres. The implant could include or be, for example, a prosthetic heart valve.

In one aspect, the inflow diameter of the stent frame in the at least partially expanded condition can be larger than the outflow diameter. Also, the stent frame can have a generally barrel shape such that the central diameter is greater than each of the inflow and outflow diameters.

The balloon, in another aspect, can be configured to exert the radially directed force through 4 to 6 atmospheres of pressure while the outflow and inflow diameters of the stent frame are equal to or smaller than the central diameter.

In another aspect, the central diameter of the stent frame in the partially, or even fully, expanded condition is at most 2 mm larger than either the inflow or the outflow diameter. The central diameter may even be as little as 1.2 mm, or even 0.8 mm, larger than either the inflow or the outflow diameters. The balloon pressure at these central diameters can, in some aspects, be from 4 to 5 atmospheres.

As another example, the central diameter of the stent frame in the at least partially expanded condition is between 0% and 2% larger than the inflow diameter at a pressure in the balloon of at least 4 atmospheres. And, the inflow diameter of the stent frame can be larger than the outflow diameter in the at least partially expanded condition.

In another aspect, the balloon may include enlarged ends. The enlarged ends are configured to extend radially past the outflow end and the inflow end of the stent frame. This may aid in retaining the stent frame on the balloon.

In other aspects, the balloon can have different materials or thicknesses for shaped expansion. For example, the balloon can have wall material with a stiffness adjacent the inflow end and the outflow end of the stent frame that is greater than a stiffness of the wall material at the central region.

In another example, the balloon can be configured to expand to a larger diameter under the central region of the stent frame than under the inflow and outflow ends of the stent frame.

The stent frame can also be configured to have regions of different stiffness. For example, the stent frame can have a lower stiffness at the central region than a stiffness adjacent the inflow and outflow ends. Or, the stent frame can have a lower stiffness adjacent the inflow and outflow ends than a stiffness at the central region.

Also included are methods of inflating the balloon and expanding a cylindrical stent. The method, for example, can include inflating a balloon, positioned in an axial opening of a generally cylindrical stent frame of an implant, to a pressure of at least 4 atmospheres. And, exerting a radial force against the cylindrical stent frame by the inflating the balloon. Then, as a result, expanding the cylindrical stent frame by the exerting the radial force an that an outflow diameter and an inflow diameter of the cylindrical stent frame are equal to or smaller than a central diameter and the central diameter is between 0% and 6% larger than the either the inflow or the outflow diameter. Expanding the generally cylindrical stent frame may include expanding the central diameter so that it is at most 2 mm, or even 1.2 mm, larger than either the inflow or outflow diameters.

DESCRIPTION OF DRAWINGS

FIGS. 2A-C depict a delivery catheter assembly for delivering a stent-mounted heart valve of one embodiment;

FIG. 8 is a table of expansion diameters of the middle, inflow and outflow ends of the valve/balloon combination shown in FIG. 7;

FIG. 9 shows a profile outline of a balloon of another embodiment with a flared end;

FIG. 10 shows the shape of a stent resulting from expansion using the balloon of FIG. 9;

FIGS. 18A-B show the expansion of a prosthetic heart valve using a conventional balloon (FIG. 18A) and an embodiment of the disclosed balloons (FIG. 18B).

DETAILED DESCRIPTION

Figure 1:
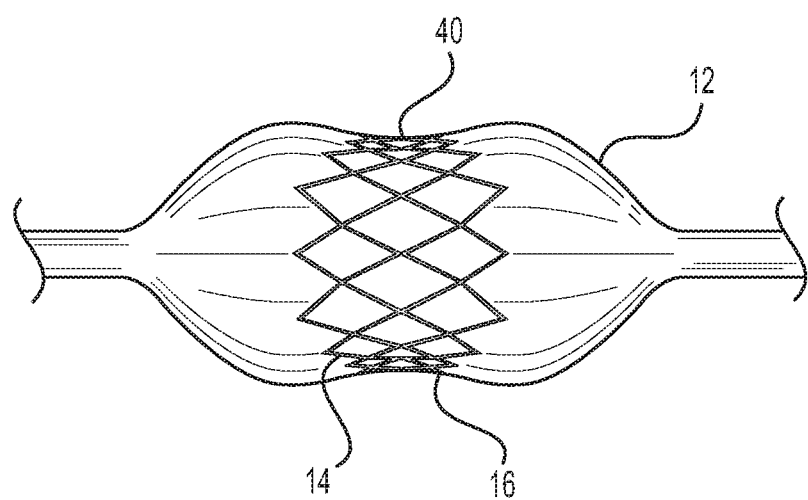
FIG. 1 is a schematic of a prior art stent-mounted prosthetic heart valve being expanded into an hourglass shape on a conventional balloon.

The following description of certain examples of a medical apparatus (e.g., a balloon catheter assembly with stent-mounted heart valve) should not be used to limit the scope of the medical apparatus. Other examples, features, aspects, embodiments, and advantages of the medical apparatus will become apparent to those skilled in the art from the following description. As will be realized, the medical apparatus is capable of additional aspects, all without departing from the spirit of the medical apparatus. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, can be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Disclosed herein are balloons for mitigating non-cylindrical or flared expansion of stents, and in particular stent-mounted tissue heart valves. For example, the balloons can be used in procedures for minimally invasive transcatheter heart valve replacement (TAVR), such as the procedures described in U.S. Pat. No. 7,175,656, which is hereby incorporated by reference in its entirety.

In conventional delivery of a balloon-expandable prosthetic heart valve, as shown in prior art FIG. 1, a balloon-expandable prosthetic heart valve comprising a stent 40 and a valve made from tissue, is mounted on a balloon 12. The balloon is expanded, resulting in the ends 14, 16 of the stent flaring outwards, forming a non-cylindrical shape. This can be problematic when the balloon 12 cannot reach the fully expanded state to urge the central region of the stent 40 into a larger diameter. Without being wed to theory, flared expansion of the stent 40 can happen because the stent structure is less stiff at the ends 14, 16 due to the lack of adjacent structure or differences in material composition or structure. The flared expansion can also be a result of the sutures anchoring the valve leaflets stiffening the supporting stent. The valve leaflets themselves can also provide some stiffness. Also, the balloon 12 can bulge outwards on the ends and provide greater expansion forces at the ends 14, 16 of the stent 40. Generally, the flared or hourglass ends 14, 16 have a diameter (for an aortic valve replacement) exceeding a central diameter of 0.50 to 0.75 mm.

Generally, disclosed herein is a stent mounted heart valve (although embodiments can include just a stent) and balloon and system of using them that can facilitate expansion—even partial expansion—of the stent mounted heart valve in a cylindrical, generally cylindrical, or near-cylindrical (e.g., barrel shaped) configuration. For example, the balloon can include differential expansion characteristics due to thickened material over its ends, allowing the center to expand more freely and form the cylindrical or barrel shape in the stent.

FIG. 2A shows one exemplary delivery apparatus 110 adapted to deliver a prosthetic heart valve 24 (e.g., a prosthetic aortic valve) to a heart. It should be understood that the delivery apparatus 110 described herein is exemplary only, and that other similar delivery systems can of course be used. The delivery apparatus 110 generally includes a steerable guide catheter 114 and a balloon catheter 32 extending through the guide catheter 114. The guide catheter 114 can also be referred to as a flex catheter, a delivery catheter, or a main catheter. The use of the term main catheter should be understood, however, to include flex or guide catheters, as well as other catheters that do not have the ability to flex or guide through a patient's vasculature.

The guide catheter 114 and the balloon catheter 32 illustrated in FIGS. 2A-2C are adapted to slide longitudinally relative to each other to facilitate delivery and positioning of prosthetic heart valve 24 at an implantation site in a patient's body, as described in detail below.

The guide catheter 114 includes a handle portion 120 and an elongated guide tube, or shaft, 122 extending from handle portion 120 (FIG. 2B). FIG. 2A shows the delivery apparatus without the guide tube 122 for purposes of illustration. FIG. 2B shows the guide tube 122 extending from the handle portion 120 over the balloon catheter 32. The balloon catheter 32 includes a proximal portion 124 (FIG. 2A) adjacent handle portion 120 and an elongated shaft 126 that extends from the proximal portion 124 and through handle portion 120 and guide tube 122. The handle portion 120 can include a side arm 127 having an internal passage which fluidly communicates with a lumen defined by the handle portion 120.

An inflatable balloon 30 is mounted at the distal end of balloon catheter 32. As shown in FIG. 2C, the delivery apparatus 110 is configured to mount the prosthetic heart valve 24 in a crimped state proximal to the balloon 30 for insertion of the delivery apparatus 110 and prosthetic heart valve 24 into a patient's vasculature, which is described in detail in U.S. Pat. No. 9,061,119 (U.S. application Ser. No. 12/247,846, filed Oct. 8, 2008), which is incorporated herein by reference. Because prosthetic heart valve 24 is crimped at a location different from the location of balloon 30 (e.g., in this case prosthetic heart valve 24 desirably is crimped proximal to balloon 30), prosthetic heart valve 24 can be crimped to a lower profile than would be possible if prosthetic heart valve 24 was crimped on top of balloon 30. This lower profile permits the surgeon to more easily navigate the delivery apparatus 110 (including crimped prosthetic heart valve 24) through a patient's vasculature to the treatment location. The lower profile of the crimped prosthetic heart valve 24 is particularly helpful when navigating through portions of the patient's vasculature which are particularly narrow, such as the iliac artery. The lower profile also allows for treatment of a wider population of patients, with enhanced safety.

FIG. 2C also illustrates an expandable sheath 1 that extends over the guide tube 122 and the balloon catheter shaft 126. The expandable sheath 1 has a lumen to guide passage of the prosthetic heart valve 24. At a proximal end the expandable sheath 1 includes a hemostasis valve that prevents leakage of pressurized blood. The delivery apparatus 110 also includes a hub 144 for connecting with the proximal end of the expandable sheath 1 (shown in FIG. 2B).

Generally, during use, the expandable sheath 1 is passed through the skin of patient (usually over a guidewire) such that the distal end region of the expandable sheath 1 is inserted into a vessel, such as a femoral artery, and then advanced to a wider vessel, such as the abdominal aorta. The delivery apparatus 110 is then inserted into the expandable sheath 1, by first inserting the nose piece 132 through the hemostasis valve at the proximal end of the sheath 1. The steerable guide tube 122 is used to advance the balloon catheter shaft 126 and prosthetic heart valve 24 through to and out of the end of the sheath 1. When the delivery apparatus 110 is at the desired procedure site, the prosthetic heart valve 24 is expanded by balloon inflation to implant the device in the patient's body. If the prosthetic heart valve 24 is positioned proximally to the balloon 30 to reduce the profile of the delivery apparatus 110 (as shown in FIG. 2C), the balloon 30 can be retracted proximally with respect to the prosthetic heart valve 24, slipping into the lumen of the prosthetic heart valve 24 to enable balloon 30 inflation and expansion of the valve 24.

Figure 3:
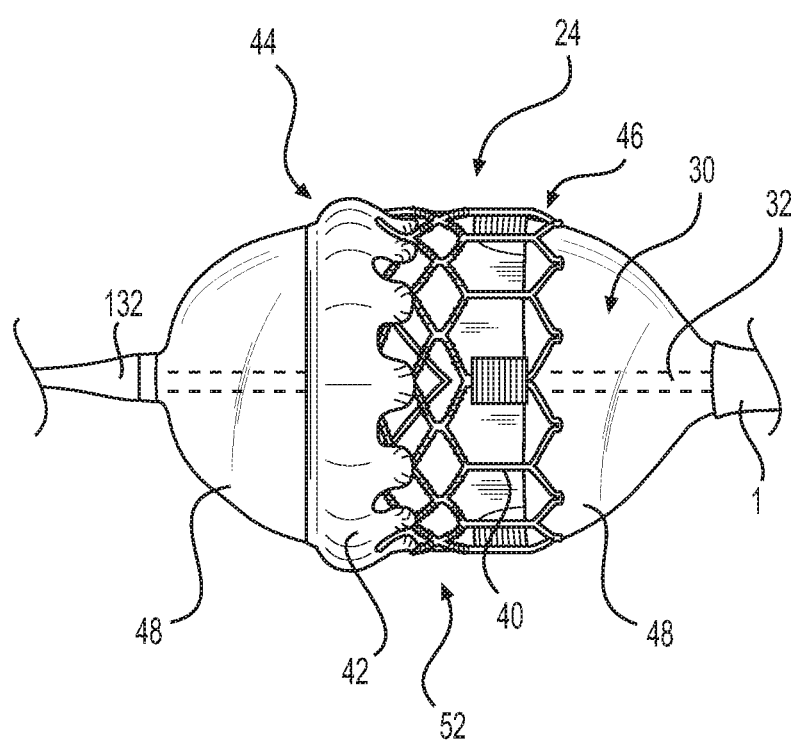
FIG. 3 is an elevation view of a stent-mounted heart valve in mid-expansion by a balloon of another embodiment.

FIG. 3 shows an at least partially expanded, generally cylindrical prosthetic heart valve 24 mounted on an at least partially inflated balloon 30. The balloon catheter 32 extends through the center of the balloon 30 to supply inflation fluid thereto. In the embodiment illustrated in FIG. 3, the prosthetic heart valve 24 includes an outer skirt 42 made from a flexible material that extends along an outside of the stent frame 40. The tissue of the prosthetic heart valve 24 includes at least one leaflet that can be attached, such as via sutures or anchors, to the stent 40. The generally cylindrical stent frame 40 has an inflow end 44 with an inflow diameter, an outflow end 46 with an outflow diameter and a central region 52 with a central diameter. The central region 52 of the stent frame 40 can have a relatively stiffer structure compared to a relatively softer structure at the inflow and outflow ends 44, 46.

The generally cylindrical stent frame 40 extends smoothly and continuously from the outflow end through the central region and to the inflow end. In some embodiments, "generally cylindrical" can encompass a "generally barrel" shape, wherein the central diameter of stent frame 40 is slightly larger than either or both of the inflow or outflow diameters. In any case, the central diameter of the disclosed stent frame 40 is not smaller than the inflow or outflow diameters of the stent frame 40.

The length of the balloon 30 shown in FIG. 3 exceeds the length of the prosthetic heart valve 24 so that ends 48 of the balloon 30 extend out of the inflow and outflow ends 44, 46 of the stent frame 40. Generally, the balloon 30 in some embodiments can avoid flaring the ends 44, 46 of the stent frame 40 by inflating in a generally "barrel" shape wherein a central region 50 of the balloon 30 expands to a larger diameter and ends 48 stay relatively smaller. The greater expansion of the central portion 50 of the balloon 30 allows more force to be exerted on the prosthetic heart valve 24 near its central region 52 so as to better coordinate expansion of the central region 50 and inflow and outflow ends 44, 46.

Figure 4:
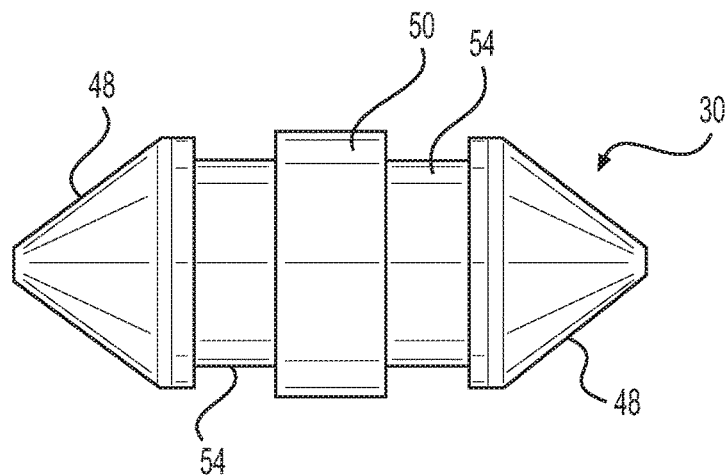
FIGS. 4-6 are schematics of shaped balloons with enlarged central portions for enhanced expansion forces on the center of stent-mounted heart valves or other cylindrical implants.
Figure 5:
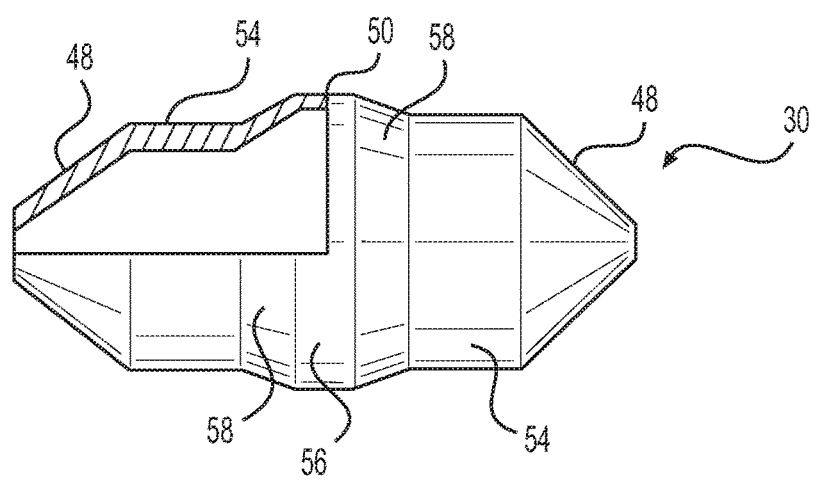
Figure 6:
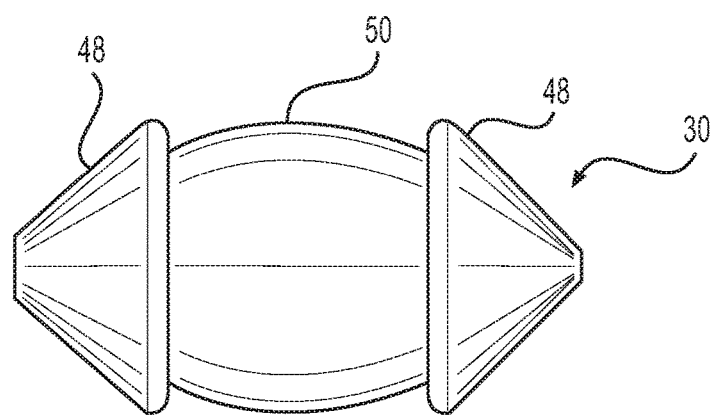

FIGS. 4-6 show exemplary embodiments of barrel shaped balloons 30. FIG. 4 shows a schematic of one embodiment of the balloon 30 including ends 48, central portion 50 and a pair of intermediate portions 54. The ends 48 are symmetrical—having a conical shape with the tip of the cone extending away from the central portion 50. The cone has about a 45 degree angle and tapers moving away from the central portion 50. Each of the ends 48 has a thin cylindrical base which steps off as the balloon 30 transitions to the intermediate portions 54.

In the embodiment of FIG. 4, the intermediate portions 54 are in between the central portion 50 and the ends 48. The intermediate portions 54 have a cylindrical shape and begin with a step-off in diameter at the end 48 and the central portion 50. The intermediate portions 54 have an axial length slightly less than an axial length of the central portion 50. The step-off from the ends 48 to the intermediate portions 54 forms a flat axially directed annular wall, helping to define the working length of balloon 30. Thus, the prosthetic heart valve 24 can be held between the flat annular walls of the ends 48 to prevent accidental migration of the prosthetic heart valve 24 during expansion.

Both of the embodiments shown in FIGS. 4 and 6 have enlarged ends 48 compared to other portions of the diameter of the balloon 30 (either the intermediate portions 54 or the central portion 50). In some examples, these enlarged ends 48 can extend radially past the outflow end and the inflow end of stent frame 40, facilitating retention of the prosthetic heart valve 24 on the balloon 30.

The central portion 50 of the embodiment of FIG. 4 has a step-up from the diameter of the intermediate portions 54 and is bracketed by the intermediate portions 54. The diameter of the central portion 50 is slightly larger than the diameter of even the cylindrical base of the ends 48. (The diameter of the cylindrical base defines the largest diameter of the ends 48.) The step-up similarly defines an axially facing, flat annular wall. Advantageously, the ability of the central portion 50 to expand to a larger diameter increases the force profile seen by the central region 52 of the stent 40 of the prosthetic heart valve 24 and thereby tends to even out the expansion of the prosthetic heart valve 24—resulting in a more cylindrical and/or slightly tapered shape.

Dimensions of the balloon 30 of FIG. 4 as molded include an axial length of 0.4 inches and a diameter of 0.946 inches for the central portion 50. The base of the ends 48 has the same 0.946 inches diameter as the central portion 50 is 0.138 inches long. The diameter of the intermediate portions 54 is 0.706 inches and their length is 0.418 inches. Thus the central portion 50 is at least 33% larger in diameter than the intermediate portions 54.

FIG. 5 shows another embodiment of the balloon 30 also including the central portion 50, intermediate portions 54 and ends 48. Similar to FIG. 4, the ends 48 have a conical shape tapering to the balloon catheter. However, the intermediate portion 54 does not have a step-off—it continues the same diameter as the base of the conical shaped ends 48. The central portion 50 includes a central plateau portion 56 bracketed by frusto-conical regions 58. The frusto-conical regions 58 define annular ramps that transition from the smaller diameter of the intermediate portions 54 to the large diameter of the central plateau portion 56. The more graduated transition between ends 48, intermediate portions 54 and central portion 50 of FIG. 5 afford a correspondingly graduated force application on the stent of the prosthetic heart valve 24. Notably, a range of transition configurations can be employed by the balloon 30 depending upon the desired profile of expansion force to help mediate the hourglass configuration affecting partially expanded transcatheter heart valves.

FIG. 5 includes a cutout showing a cross section of the wall (upper left side of the image) of balloon 30. The wall is thinner in central portion 50, which facilitates greater expansion in that area.

Dimensions of the balloon of FIG. 5 as molded include an axial length of 0.4 inches and a diameter of 0.946 inches for the central portion 50. The intermediate portions 54 have a diameter of 0.8 inches. The central portion 50 diameter is thus at least 18% larger than the diameter of the intermediate portions 54. The intermediate portions 54 have a 0.306 inch length. The frusto-conical regions 58 have a length of 0.209 inches.

FIG. 6 shows yet another embodiment of the balloon 30. The ends 48 have the same conical shape with step off as the balloon in FIG. 4 to bracket the heart valve 24. The balloon 30 has a central portion 50 which has a smooth bulging, barrel shape extending between the two ends 48. At its center, the central portion 50 of FIG. 4 has a smaller diameter than the base of the ends 48. The balloon 30 of FIG. 6 thus has enhanced abilities to retain the heart valve 24 even at the extreme inflation diameter. And, the smooth barrel shape of the central portion 50 exerts a correspondingly smooth force profile against the inside of the heart valve 24 during inflation.

The dimensions of the balloon of FIG. 6 as molded include an axial length of 0.986 inches and a 0.652 inches maximum diameter and 0.554 or 0.575 inches minimum diameter for the central portion 50. Thus the maximum diameter is at least 13% larger than the minimum diameter of the central portion 50. The largest diameter of the ends is 1.158 inches.

The balloons 30 disclosed herein can be shaped by different approaches alone or in combination. For example, different materials with varying stiffness (less stiff at the central portion 50) might be used to enhance the central portion's 50 diameter. Materials include PET, nylon, PEBAX (polyether block amid) or other polymers with adaptable or selectable ranges of stiffness. In some embodiments, the balloon 30 can have a wall material that is relatively stiff under the inflow and outflow ends 44, 46 of the stent frame 40, and relatively soft under the central region 52 of the stent frame 40. Or, the thickness of the wall of the central portion 50 could be reduced (as shown in FIG. 5) to allow its expansion to the larger diameter. Another approach would be to expand the balloon 30 into a heated die with the desired end-shape. Yet another approach would be to apply coatings or additional layers, such as flexible, knitted sleeves, at strategic locations on the balloon's surfaces.

Advantageously, the barrel shaped balloons 30 disclosed herein work well with skirted prosthetic heart valve 24 because the skirt provides an outer restraint to overexpansion. Modification of the balloon 30 to exert more force at its central portion 50 also increases its potential end diameter. Delivery of other medical implants, such as stents, can also benefit from use of a skirt or other outer covering or restraint to provide an end point to the diameter of the implant's expansion.

The enlarged central portion of the balloon advantageously raises the retention forces of the implant and reduces the chance of migration of the implant. Also, the shaped balloons described herein allow control of the amount of flare in the final expanded shape of the implant. For example, the physician can determine whether to inflate the balloon so as to create a cylindrical shape in the implant or to keep the flare on the ends (or to enhance the flare as disclosed below). Also, the physician can stop inflation of the balloon at a lower diameter than nominal diameter of the implant—protecting from risk of annular rupture. Also, reducing the flare at the ends of the implant reduces chances that the stent frame apices will cause conduction system disturbances and/or tissue perforation at the inflow and outflow ends.

Figure 7:
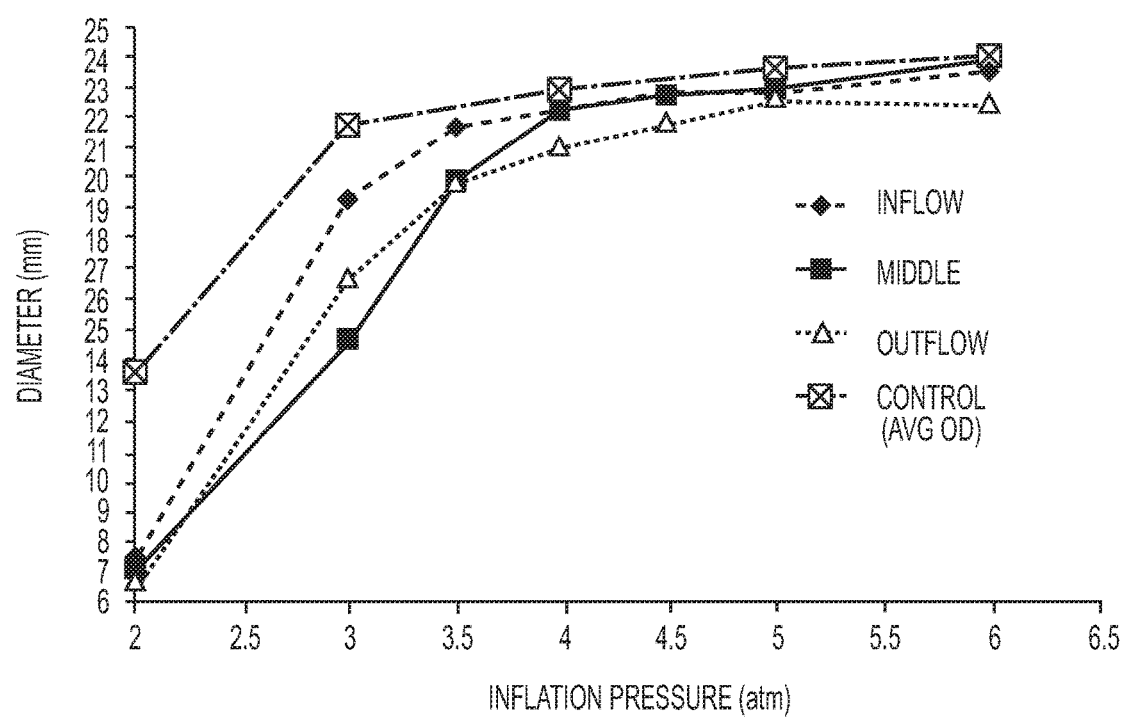
FIG. 7 is a graph of conventional stent-mounted heart valve expansion diameter compared to the inflow, outflow and middle diameter of an embodiment of the valve/balloon combination.
Figure 18A:
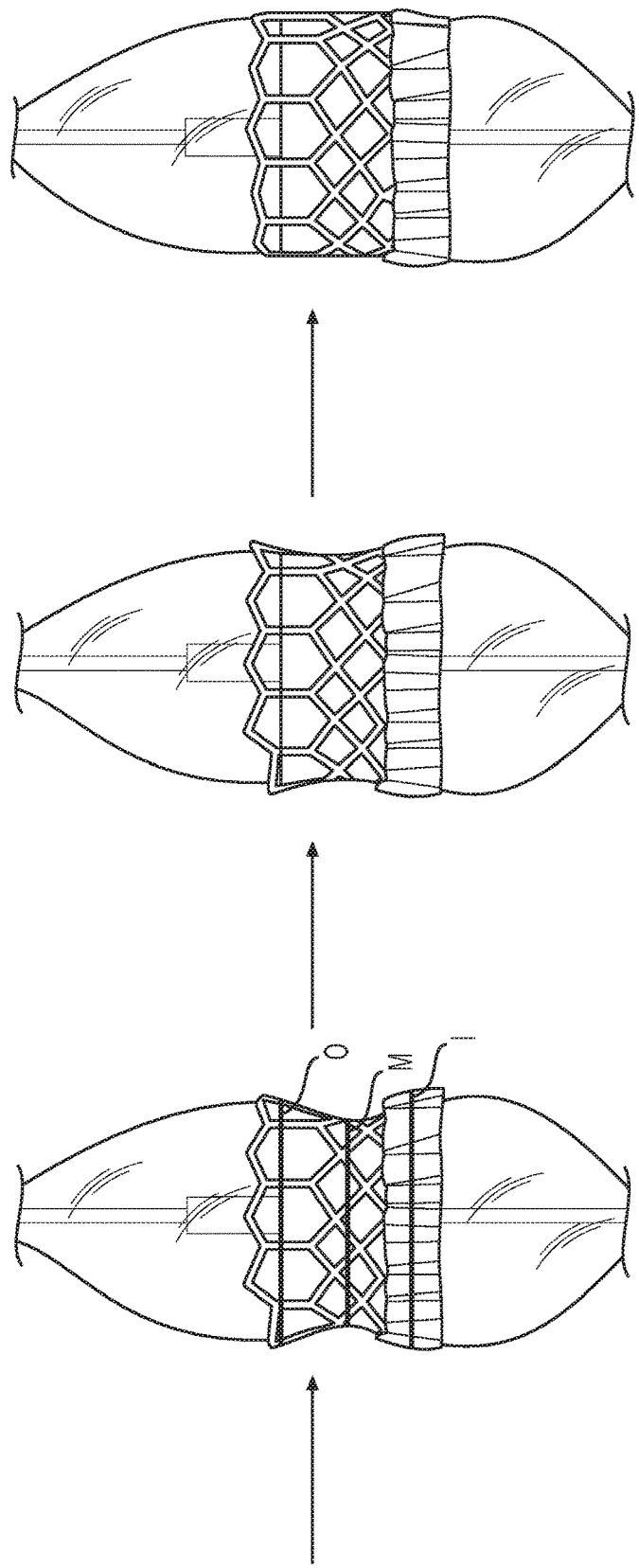

Experiments were run comparing the inflation profile of a conventional balloon and stent mounted prosthetic heart valve against an embodiment of the shaped balloon/valve combinations disclosed herein. FIGS. 18A-B show the conventional balloon/valve combination opening with a flared shape (FIG. 18A) and shaped balloon/valve combination (FIG. 18B) opening with a generally cylindrical or barrel shape, with inflation pressures increasing from left to right. FIG. 7 provides a graph of conventional stent-mounted heart valve expansion diameter compared to the inflow, outflow and middle diameter of an embodiment of the shaped balloon/valve combination described herein. FIG. 7 shows the average outer diameter (box with X) during inflation of the conventional balloon/prosthetic heart valve combination as compared to the outer diameter of the inflow (diamond), outflow (triangle) and middle (plain box) portions of the shaped balloon/prosthetic heart valve combination disclosed herein, as inflation pressures increase from 2 to 6 atmospheres (atm).

Notably, for the shaped balloon/valve combination of the tested embodiment, the middle diameters at 4, 4.5 and 5 atmospheres were about equal to or exceeded the inflow and outflow diameters. FIG. 8 is a table showing the middle diameter (M) (or central diameter) of the shaped balloon/valve combination as a percentage of the inflow (I) and outflow (O) diameters. The numbers are based on the data from the graph of FIG. 7. Thus, a positive percentage is the percentage the middle diameter exceeds the inflow or outflow diameters at various inflation pressures. Notably, above 4 atmospheres the percentages are either 0% (no difference), or positive up to about 6%, indicating a cylindrical or barrel shaped implant. Particularly, the central diameter M is from 0% to 6% larger than the outflow diameter O at a pressure in the balloon of at least 4 atmospheres.

The actual difference measured between the central diameter M and the outflow diameter O for this tested embodiment was 1.2 mm at 4 atmospheres, 0.8 mm at 4.5 atmospheres, and 0.3 mm at 5 atmospheres (based on the data shown in FIG. 8). These actual measured difference values are based on a single tested embodiment. These values are dependent on the overall size, construction, and materials of the valve and balloon and therefore may not be representative of all embodiments. For example, some embodiments of the valve and balloon combination could result in a difference of up to 2 millimeters between the central diameter M and the inflow or outflow diameters I or O. Furthermore, various adjustments to the materials or construction of the prosthetic heart valve 24 or the balloon 30 could be made to allow for a generally cylindrical or barrel shaped expanded prosthetic heart valve 24 at pressures lower than 4 atmospheres. Also, the inflow diameter of the tested embodiment is slightly larger than the outflow diameter (as shown by the data in FIG. 8). However, some applications may exist that call for an embodiment with an outflow diameter that is larger than the inflow diameter.

The balloons 30 described herein can be used to expand the prosthetic heart valve 24 into cylindrical or barrel shapes for deployment within ranges of pressures. For example, one method of valve implantation includes positioning the balloon 30, with the prosthetic heart valve 24 mounted thereon, within a native heart valve using the delivery apparatus 110. The balloon 30 is inflated to a pressure of at least 4 atmospheres while it is positioned in the native heart valve. Inflating the balloon 30 exerts an outward radial force against the cylindrical stent frame 40 of the prosthetic heart valve 24 so that an outflow diameter and inflow diameter are equal to or smaller than the central (or middle) diameter. For example, the central diameter can be between 0% and 6% larger than the outflow diameter.

The expansion method could also be performed to hit certain tolerances between the central, outflow and inflow diameters. In this manner, then, the method can be used to "tune" the prosthetic heart valve's 24 shape. It should be noted that the balloon designs could be reshaped to be more or less aggressive than the tested embodiment depending upon the desired progression and ranges. In another embodiment, the inflow end 44 may have a diameter smaller than the middle section diameter and the middle section diameter may have a smaller diameter than the outflow end 46 diameter. For example, the diameter of the stent from the inflow end 44 through the middle section and to the outflow end 46 may progressively increase.

In another embodiment, the balloon 30 can be contoured to do the opposite—expand one or both of the inflow and outflow ends 44, 46 of the stent 40 to a larger diameter than the middle section. For example, the balloon 30 can be pre-shaped to give it contours to increase the outward force applied to the inflow and outflow ends 44, 46 of the stent to be more than the outward force applied to the central region 52 of the stent 40.

For this embodiment, without being wed to theory, in certain situations flaring the ends of the stent aids in long-term leaflet durability, as well as sealing and seating of the stent 40 during deployment. In particular, flaring the outflow end 46 of the stent 40 provides additional room for the valve leaflets to open without coining into contact with the stent frame 40—thus improving the effective orifice area (EOA) of the implanted valve.

Flaring of both ends 44, 46 may also press the stent frame 40 up against the annulus which can aid in preventing paravalvular leakage. In addition, flaring the ends 44, 46 can prevent the prosthetic heart valve 24 from migrating under backpressure against the valve. These flared stents need not have the aforementioned disadvantages depending upon positioning of the flares—they can be further out for some applications or closer in for other applications.

These shaped balloons 30 with enlarged ends can also be combined with stents 40 configured to follow the balloon shapes. For example, the stents may also be shaped with enlarged ends in the crimped configuration to facilitate expansion by the balloon into the final, flared shape. The crimped stent may, for example, have a consistent diameter through the central region but pass an inflection point where it begins to flare out into a larger diameter near its ends. Similarly, for barrel-shaped balloon embodiments, the crimped stent may be shaped with tapered ends that have a smaller diameter than the central region. Thus, the central area of the crimped stent will be more likely to expand to a larger diameter than the ends with the enhanced pressure of the central area of the barrel-shaped balloon.

Further, the stents may be provided with selective areas of higher and lower stiffness that correspond with the balloon shapes. For example, the density of stent struts, strut material and/or strut thickness may be adapted to allow easier expansion within selected circumferential bands. For the flared balloon, the ends of the stents may have more struts with a lower thickness, and/or fewer interconnections, enhancing the tendency of the stent to flare at the ends with the additional force supplied by the flared balloon. For the barrel-shaped balloon, the ends of the stents could be provided with thicker, fewer and/or more interconnected struts to reduce the tendency of the inflow and outflow ends to expand along with the reduced inflation pressure being supplied at the ends from the barrel-shaped balloon.

Other useful balloon shapes include the balloon 30 shown in FIG. 9 that has a conical flare 60 positioned to induce a similar inflow end 44 conical flare 64 in the stent 40 during expansion, as shown in FIG. 10. The stent shape of FIG. 10 is particularly useful to mediate paravalvular leaks and helps with seating the prosthetic heart valve 24 in an aortic valve. The conical flare 60 could also be positioned at the outflow end of the balloon 30 so the stent frame 40 would flare at the outflow end 46 to enhance the ability of the leaflets to expand without wear and enhance EOA of the implanted valve, as noted above.

Figure 11:
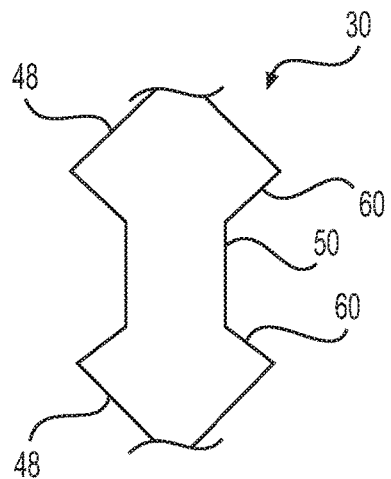
FIG. 11 shows a profile outline of a balloon of another embodiment with two flared ends.
Figure 12:
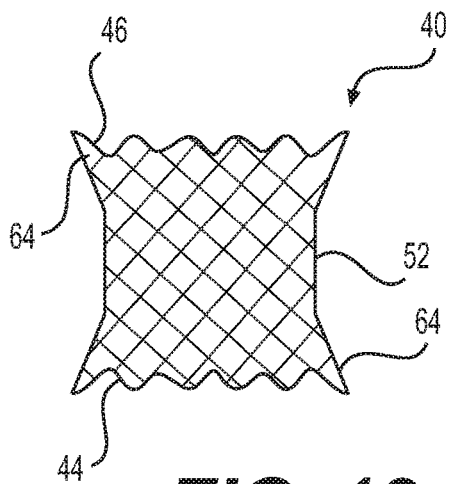
FIG. 12 shows the shape of a stent resulting from expansion using the balloon of FIG. 11.

FIG. 11 shows a balloon 30 with a conical flare 60 positioned at both ends 48 of the balloon. This induces similar conical flares 64 at both the inflow and outflow ends 44, 46, of the expanded stent as shown in FIG. 12. Flaring both ends combines the advantages of both inflow and outflow positioned flares described above.

Figure 13:
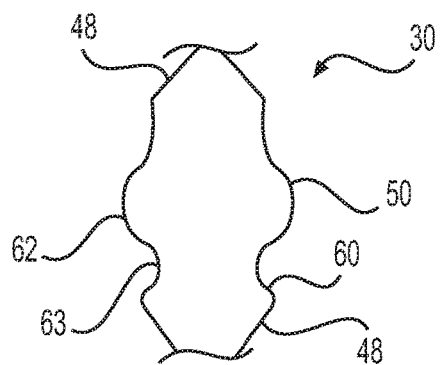
FIG. 13 shows a profile outline of a balloon of another embodiment with one flared end and a central belly or bulge.
Figure 14:
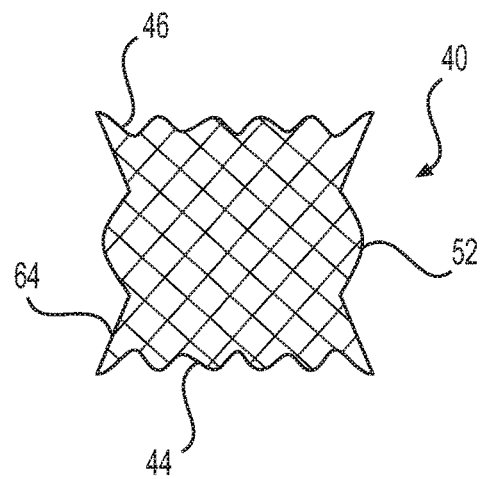
FIG. 14 shows the shape of a stent resulting from expansion using the balloon of FIG. 13.

FIG. 13 shows a balloon 30 with a conical flare 60 positioned at the inflow end of the balloon 30 and a belly 62 positioned in the middle of the balloon 30. The belly 62 is separated from the conical flare 60 by a waist 63. As shown in FIG. 14, the resulting stent shape includes the flare on the inflow end 44 to mediate paravalvular leaks, the waist 63 to aid in valve seating and the belly 62 to provide more room for the tissue valve 36 positioned within the stent. The waist 63 is positioned at the annulus of the native heart valve to align and seat the prosthetic heart valve 24 during expansion. A second outflow end flare could be induced into the stent 40 also.

Figure 15:
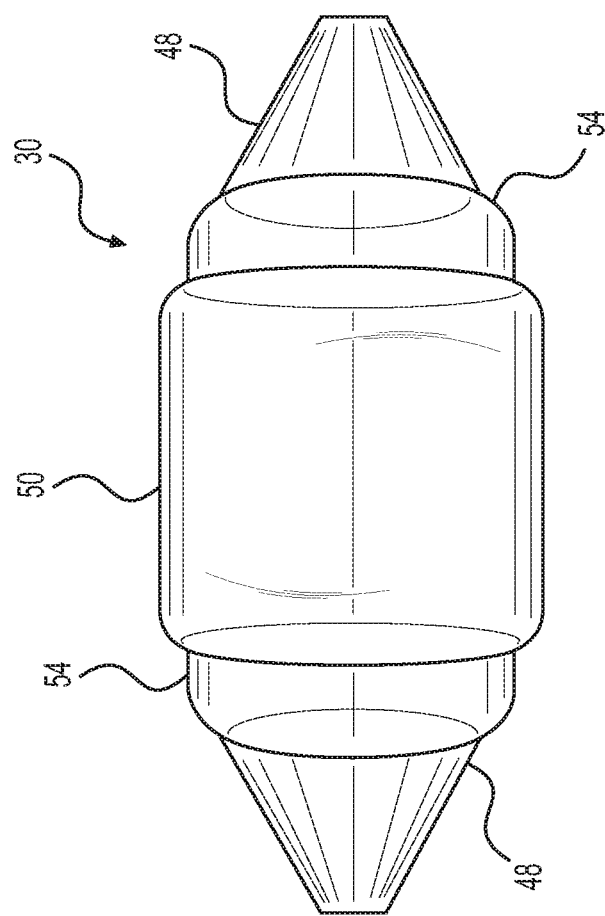
FIG. 15 is a perspective view of a balloon of another embodiment.

FIG. 15 shows another embodiment of balloon 30 wherein the central portion 50 is the largest diameter, the intermediate portions 54 the next largest diameter and then an additional step down to the ends 48 which have a conical shape. The central portion 50 is also distinguished by having a length that is at least 3 or 4 times the length of one of the intermediate portions 54.

During application, the shaped balloons can be expanded within stents that have cylindrical shapes when crimped and expand them selectively to have the disclosed features—the flares, waist, belly, etc. Thus the same methods can be applied as described above, but with different areas of enhanced balloon features. The stents 40 can also be selectively weakened at the location of the flares and belly to enhance expansion via the shaped balloons.

Figure 16:
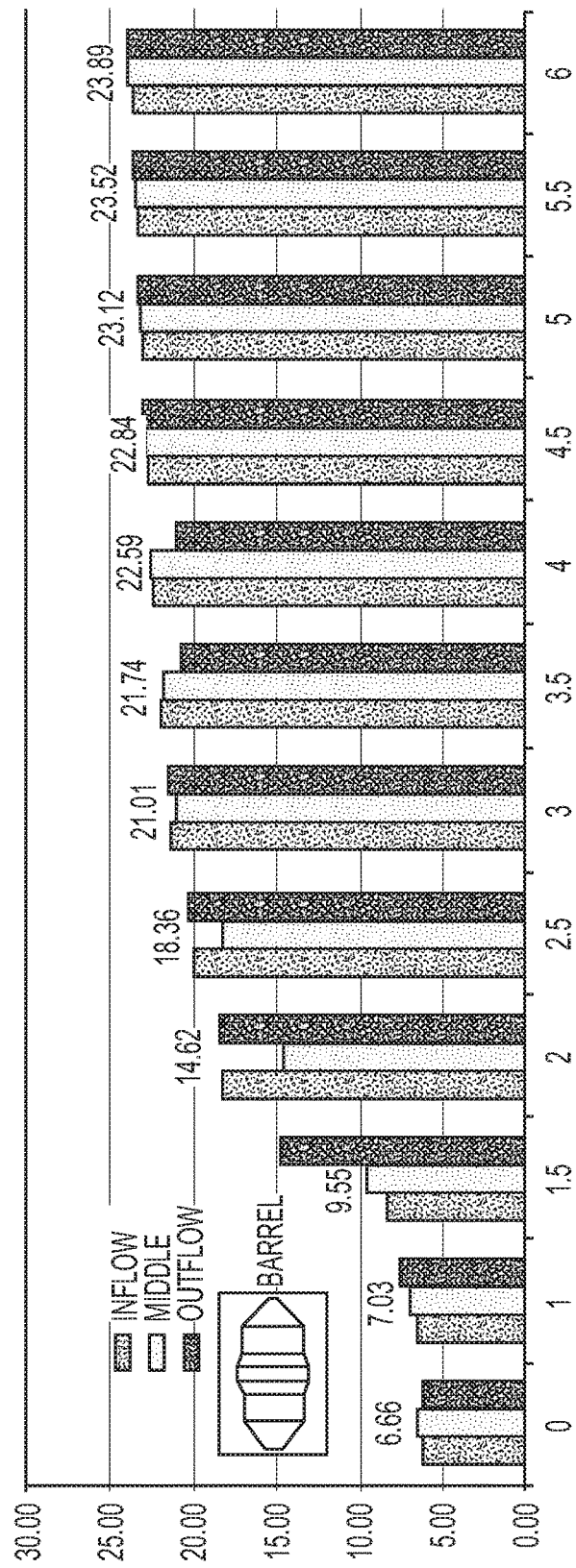
FIG. 16 is a graph of an expansion profile of a prosthetic heart valve mounted on the balloon of FIG. 5.

FIG. 16 shows a bar graph of additional data collected on the diameters of a prosthetic heart valve 24 expanded by a balloon 30 similar to that shown in FIG. 5. Data is provided up to a pressure of 6 atmospheres. Notably, the middle diameter exceeds the outflow diameter starting at about 3.5 atmospheres and then at 4 atmospheres exceeds both the inflow and outflow diameters. The barrel shape is maintained at 4 atmospheres. At higher pressures of about 4.5 atmospheres and above, the inflow, outflow and middle diameters are for practical purposes equal, forming a cylindrical prosthetic heart valve 24.

Figure 17:
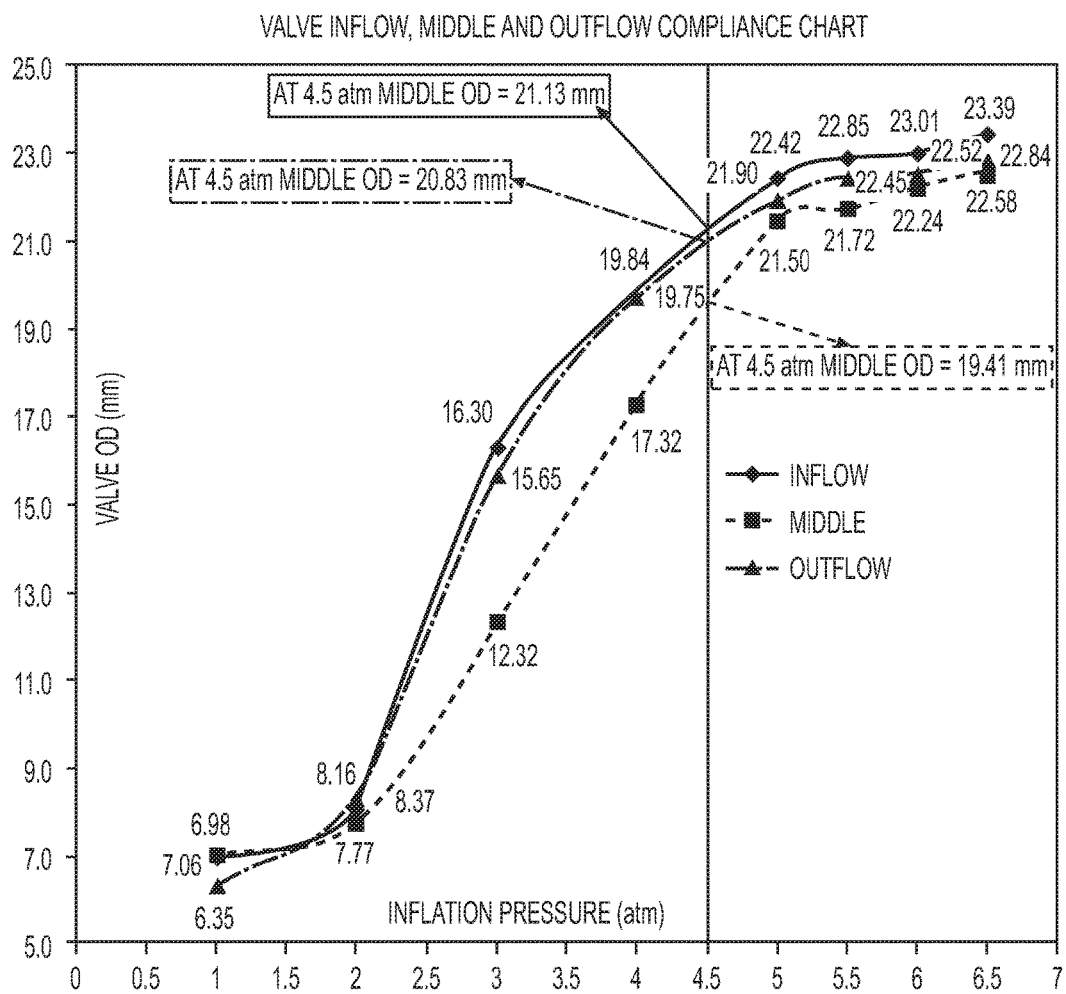
FIG. 17 is another graph of an expansion profile of a prosthetic heart valve mounted on the balloon of FIG. 5.

FIG. 17 shows a separate example of data collected on the diameters of a prosthetic heart valve 24 during the inflation of balloon 30. Inflow, middle, and outflow diameters are individually tracked. In this example, the inflow and outflow diameters exceed the middle diameter at 2 atmospheres and greater. However, the difference between the end (both out flow and inflow) diameters versus the middle diameter of the valve lessens at the higher atmospheric pressures, indicative of the barrel-like balloon 30 shape underneath.

Although the disclosure has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments. In addition, while a particular feature of the disclosure may have been described above with respect to only one or more of several illustrated embodiments, such feature may be combined with one or more other features of the other embodiments, as may be desired and advantageous for any given or particular application.

What is claimed is:

1. A system comprising:
   a prosthetic heart valve having a generally cylindrical stent frame with an axial opening and having an inflow end defining an inflow diameter, an outflow end defining an outflow diameter and a central region defining a central diameter, the central region between the inflow end and outflow end; and
   a balloon extending through the axial opening and configured to expand and exert a radially directed force against the stent frame so that the outflow diameter and inflow diameter are smaller than the central diameter in an at least partially expanded condition;
   wherein the stent frame in the at least partially expanded condition has a generally barrel shape such that the central diameter of the stent frame is larger than either the inflow or the outflow diameter of the stent frame by up to 6% in the at least partially expanded condition and at a pressure in the balloon of at least 4 atmospheres.

2. A system of claim 1, wherein the inflow diameter of the stent frame in the at least partially expanded condition is larger than the outflow diameter.

3. A system of claim 1, wherein the outflow diameter of the stent frame in the at least partially expanded condition is larger than the inflow diameter.

4. A system of claim 1, wherein the balloon is configured to exert the radially directed force through 4 to 6 atmospheres of pressure while the outflow and inflow diameters of the stent frame are smaller than the central diameter.

5. A system of claim 1, wherein the central diameter of the stent frame in the at least partially expanded condition is at most 2 mm larger than either the inflow or the outflow diameters.

6. A system of claim 5, wherein the pressure in the balloon is from 4 to 5 atmospheres.

7. A system of claim 1, wherein the central diameter of the stent frame in the at least partially expanded condition is at most 1.2 mm larger than either the inflow or outflow diameters.

8. A system of claim 1, wherein the central diameter of the stent frame in the at least partially expanded condition is at most 0.8 mm larger than either the inflow or the outflow diameters.

9. A system of claim 1, wherein the central diameter of the stent frame in the at least partially expanded condition is between 0% and 2% larger than the inflow diameter at the pressure in the balloon of at least 4 atmospheres.

10. A system of claim 9, wherein the inflow diameter of the stent frame in the at least partially expanded condition is larger than the outflow diameter.

11. A system of claim 1, wherein the balloon further includes enlarged ends configured to extend radially past the outflow end and the inflow end of the stent frame so as to retain the implant on the balloon.

12. A system of claim 1, wherein the balloon has a wall material with a stiffness adjacent the inflow end and outflow end of the stent frame that is greater than a stiffness of the wall material at the central region.

13. A system of claim 1, wherein the balloon is configured to expand to a larger diameter under the central region of the stent frame than under the inflow and outflow ends of the stent frame.

14. A system of claim 1, wherein the stent frame is configured to have regions of different stiffness.

15. A system of claim 14, wherein the stent frame has a lower stiffness at the central region than a stiffness adjacent the inflow and outflow ends.

16. A system of claim 14, wherein the stent frame has a lower stiffness adjacent the inflow and outflow ends than a stiffness at the central region.

17. A method comprising:
inflating a balloon, positioned in an axial opening of a generally cylindrical stent frame of a prosthetic heart valve, to a pressure of at least 4 atmospheres;
exerting a radial force against the cylindrical stent frame by the inflating the balloon; and
expanding the generally cylindrical stent frame to an at least partially expanded condition having a generally barrel shape by exerting the radial force so that an outflow diameter and an inflow diameter of the stent frame are smaller than a central diameter of the stent frame, the central diameter being larger than either the inflow or the outflow diameter by up to 6%.

18. The method of claim 17, wherein expanding the generally cylindrical stent frame includes expanding the generally cylindrical stent frame so that the central diameter is at most 2 mm larger than either the inflow or the outflow diameters in the at least partially expanded condition.

19. The method of claim 17, wherein expanding the generally cylindrical stent frame includes expanding the generally cylindrical stent frame so that the central diameter is at most 1.2 mm larger than either the inflow or the outflow diameters in the at least partially expanded condition.

* * * * *